United States Patent [19]

Adelstein et al.

[11] Patent Number: 4,721,718

[45] Date of Patent: Jan. 26, 1988

[54] 2-[(IMIDAZO[1,2-A]PYRIDIN-3-YLMETHYL)SULFINYL]-1H-BENZIMIDAZOLES USEFUL IN THE TREATMENT AND PREVENTION OF ULCERS

[75] Inventors: Gilbert W. Adelstein, Evanston; Alan E. Moormann, Skokie; Chung-Hwai Yen, Prospect Heights, all of Ill.

[73] Assignee: G. D. Searle & Co., Chicago, Ill.

[21] Appl. No.: 897,687

[22] Filed: Aug. 18, 1986

[51] Int. Cl.$^4$ .................. A61K 31/44; C07D 471/04
[52] U.S. Cl. ................................. 514/300; 546/121
[58] Field of Search ......................... 546/121; 514/300

[56] References Cited

U.S. PATENT DOCUMENTS

| 4,045,564 | 8/1977 | Berntsson et al. | 424/263 |
|---|---|---|---|
| 4,182,766 | 1/1980 | Krassó | 424/263 |
| 4,248,880 | 2/1981 | Krassó | 424/263 |
| 4,255,431 | 3/1981 | Junggren | 424/263 |
| 4,327,102 | 4/1982 | Crossley | 424/263 |
| 4,337,257 | 6/1982 | Junggren | 424/263 |
| 4,359,465 | 11/1982 | Ruwart | 426/263 |
| 4,394,509 | 7/1983 | Crossley | 546/339 |
| 4,405,563 | 8/1977 | Berntsson et al. | 424/263 |
| 4,472,409 | 9/1984 | Senn-Bilfinger | 424/263 |

FOREIGN PATENT DOCUMENTS

| 903128 | 12/1985 | Belgium . |
|---|---|---|
| 127763 | 12/1984 | European Pat. Off. . |
| 130729 | 1/1985 | European Pat. Off. . |
| 3415971 | 8/1984 | Fed. Rep. of Germany . |
| 416649 | 1/1981 | Sweden . |
| 2134523 | 8/1984 | United Kingdom . |
| 2137616 | 8/1984 | United Kingdom . |

OTHER PUBLICATIONS

Im et al., J. of Biol. Chem., 250(8), pp. 4591–4597 (1985).

J. G. Spenny, "Biochemical Mechanisms of Acid Secretion by Gastric Parietal Cells", *J. Clin. Gastro.*, 5 (suppl. 1), 7–15 (1983).

B. Beilenson & F. M. Hamer, "Thiazenocyanines, Part I. Carbocyanins Containing the 2:4-Benzthiazine Nucleus," *J. Chem. Soc.*, 98–102 (1942).

J. Chandra Rajan & L. Klein, "Determination of Inorganic Phosphorus in the Presence of Organic Phosphorus . . . ," *Anal. Biochem.*, 72, 407–412 (1976).

*Primary Examiner*—Henry R. Jiles
*Assistant Examiner*—Bernard I. Dentz
*Attorney, Agent, or Firm*—Richard E. L. Henderson; Paul D. Matukaitis

[57] ABSTRACT

This invention relates to 2-[(imidazo[1,2-a]pyridin-3-ylmethyl)sulfinyl]-1H-benzimidazoles that are useful in the treatment and prevention of ulcers.

12 Claims, No Drawings

2-[(IMIDAZO[1,2-A]PYRIDIN-3-YLMETHYL)SULFINYL]-1H-BENZIMIDAZOLES USEFUL IN THE TREATMENT AND PREVENTION OF ULCERS

BACKGROUND OF THE INVENTION (a) Field of the Invention

This invention relates to compounds that are useful in the treatment and prevention of ulcers. More particularly, this invention relates to certain 2-[(imidazo[1,2-a]pyridin-3-ylmethyl)sulfinyl]-1H-benzimidazoles that inhibit $(H^+ + K^+)$-ATPase obtained from gastric mucosa and thus inhibit acid secretion by parietal cells of the stomach through inhibition of $(H^{30} + K^+)$-ATPase. For review, see, e.g., J. G. Spenney, "Biochemical Mechanisms of Acid Secretion by Gastric Parietal Cells," *J. Clin. Gastro.*, 5 (Suppl. 1), 7-15 (1983). In addition, some of the compounds of this invention may also exert cytoprotective activity. For review of cytoprotection, see, e.g., U.S. Pat. No. 4,359,465.

(b) Prior Art

The compound of Formula (A), 2-[imidazo[1,2-a]pyridin-2-ylmethyl)sulfinyl]-1H-benzimidazole, (See Example 4 herein), has been disclosed.

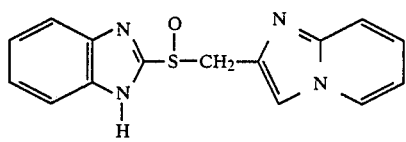
(A)

Compound (A) differs structurally from the compounds of this invention in the position of attachment of the sulfinylmethyl function to the imidazo[1,2-a]pyridine ring system. Moreover, as shown in Table I below compound (A) differs biologically from compounds of this invention in not inhibiting $(H^+ + K^+)$-ATPase activity, a biological property characteristic of the compounds of this invention.

Certain other heterocyclylalkylsulfinylbenzimidazoles have been disclosed as gastric acid secretion inhibitors. See U.S. Pat. Nos. 4,472,409, 4,394,509, 4,337,257, 4,327,102, 4,255,431, 4,045,564, and 4,045,563; British patent No. 2,134,523; German Offenlegungsschrift No. 3,415,971, and Swedish patent No. 416649. Some heterocyclylalkylsulfinylbenzimidazoles have also been disclosed as cytoprotective agents. See U.S. Pat. No. 4,359,465. Compounds of Formula (B) are illustrative of the heterocyclylalkylsulfinylbenzimidazole compounds disclosed in these patents:

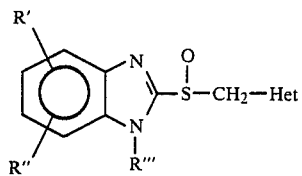
(B)

wherein R' and R" represent hydrogen, alkyl, halogen, trifluromethyl, cyano, carboxy, hydroxy, acyl, and the like; R''' represents hydrogen, alkyl, acyl, alkoxysulfonyl, and the like; and Het represents heterocyclic groups containing at least one endocyclic (ring) nitrogen. No compound disclosed in these patents includes an imidazo[1,2-a]pyridine ring system, a structural feature characteristic of the compounds of the present invention.

Heterocyclylalkylsulfinylnaphth[2,3-d]imidazoles have also been disclosed as gastric acid secretion inhibitors. See U.S. Pat. Nos. 4,248,880 and 4,182,766. The compounds disclosed in these patents are related to compounds of Formula (B), except for having a substituted naphth[2,3-d]imidazole group instead of the benzimidazole group. Similarly, other heterocyclylalkylsulfinylbenzimidazoles having a ring fused to the benzimidazole group have been disclosed as gastric acid secretion inhibitors and cytoprotective agents. See European patent application Nos. 130,729 and 127,763. The presence of the naphth[2,3-d]imidazole group and the absence of an imidazopyridine ring system distinguishes these compounds from the compounds of the present invention.

Benzylsulfinylbenzimidazoles have also been disclosed as antiulcer agents. Belgian patent No. 903,128. No compounds disclosed in the Belgian patent contain an imidazopyridine ring system, a structural feature characteristic of the compounds of this invention.

SUMMARY OF THE INVENTION

The invention relates to compounds of Formula I:

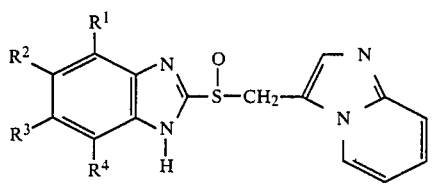
I or the pharmaceutically acceptable acid addition salts thereof; or the pharmaceutically acceptable base addition salts thereof; wherein $R^1$, $R^2$, $R^3$, and $R^4$ are independently:
(a) hydrogen;
(b) $C_1-C_6$ alkyl;
(c) $C_1-C_6$ alkoxy;
(d) fluorinated $C_1-C_4$ alkyl; or
(e) halogen.

Although the structure shown for Formula I indicates one tautomeric form, it is understood that this representation is for convenience only and that the scope of this invention includes as equivalents all tautomeric forms of the compounds of this invention.

The term "$C_1-C_6$ alkyl" refers to straight or branched chain alkyl groups having from 1 to 6 carbon atoms, also referred to as lower alkyl. Examples of $C_1-C_6$ alkyl are methyl, ethyl, propyl, butyl, pentyl, hexyl, and the isomeric forms thereof.

The term "$C_1-C_6$ alkoxy" refers to straight or branched chain alkoxy groups having from 1 to 6 carbon atoms. Examples of $C_1-C_6$ alkoxy are methoxy, ethoxy, propoxy, butoxy, pentoxy, hexoxy, and the isomeric forms thereof.

The term "fluorinated $C_1-C_4$ alkyl" refers to straight or branched chain alkyl groups in which one or more hydrogen atoms are replaced with fluroine atoms. Examples of $C_1-C_4$ fluorinated alkyl are fluoromethyl, difluoromethyl, trifluoromethyl, 1- or 2-fluoroethyl, 1,1-difluoroethyl, 2,2,2-trifluoroethyl, perfluoroethyl; other similarly monofluorinated, polyfluorinated, and perfluorinated ethyl, propyl, and butyl groups; and the isomeric forms tbereof.

Examples of halogen are fluorine, chlorine, bromine, and iodine.

The term "pharmaceutically acceptable acid addition salt" refers to a salt prepared by contacting a compound of Formula I with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts.

The term "pharmaceutically acceptable base addition salt" refers to a salt prepared by contacting a compound of Formula I with a base whose cation is generally considered suitable for human consumption. Examples of pharmacologically acceptable base addition salts include lithium, sodium, potassium, magnesium, calcium, titanium, ammonium, alkylammomium, dialkylammomium, trialkylammomium, tetraalkylammomium, and guanidinium salts.

DESCRIPTION OF THE INVENTION

The compounds of this invention may be prepared using the methods illustrated in the following Schemes. Unless otherwise specified, the various substituents are defined as for Formula I, above. Schemes A and B illustrate a preferred method for preparing the sulfoxide compounds of this invention, Formula I, by way of thio intermediates of Formula VIII that are formed by S-alkylation of a 2-mercaptobenzimidazole of Formula VII with a 3-(halomethyl)imidazo[1,2-a]pyridine of Formula VI (where X is a halogen). Scheme A illustrates the preparation of the 3-(halomethyl)imidazo[1,2-a]pyridines of Formula VI.

SCHEME A

Cyclization of 2-aminopyridine, Formula II, forms the unsubstituted imidazo[1,2-a]pyridine ring system. A preferred cyclization method involves reaction of 2-aminopyridine with a haloacetaldehyde, preferably chloroacetaldehyde, in a suitable solvent.

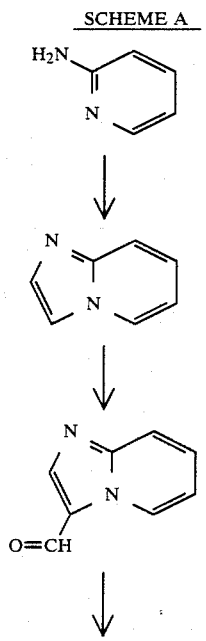

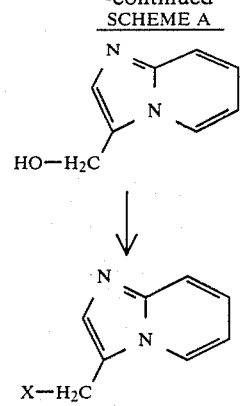

Suitable solvents for cyclization are liquids in which reactants may be dissolved or suspended but which are otherwise chemically inert. Examples of suitable solvents include water; organic liquids, preferably alcohols; mixtures of water and water-miscible organic liquids; and other such solvents known in the art. A preferred solvent is water. Cyclization may be performed with a suitable base added or, preferably, without such a base. Suitable bases for cyclization are chemical compounds that are sufficiently basic to promote the cyclization but which do not themselves form significant quantities of byproducts by reaction with reactants or desired products. Examples of suitable bases include alkali metal carbonates or bicarbonates, such as lithium, sodium, or potassium carbonate, or lithium, sodium, or potassium bicarbonate; and tertiary amines, such as triethylamine, tributylamine, N-methylmorpholine, and the like. Preferred bases include alkali metal bicarbonates, preferably sodium bicarbonate. The imidazo[1,2-a]pyridine thus formed may be isolated by methods known in the art, preferably by solvent-solvent extraction or chromatography, and purified by methods known in the art, preferably by distillation at reduced pressure.

Substitution at the 3-position of imidazo[1,2-a]pyridine may be effected be a Vilsmeier-Haack or similar aldehyde-forming reaction. Preferred reaction conditions include using a mixture of dimethylformamide and phosphorus oxychloride. The resultant aldehyde of Formula IV may then be reduced to the corresponding 3-(hydroxymethyl)imidazo[1,2-a]-pyridine of Formula V using reduction methods known in the art. Examples of reduction methods include catalytic hydrogenation and reaction with any of various active hydride reducing agents, such as sodium or lithium borohydride, lithium aluminum hydride, various boranes, and the like. A preferred reduction method employs sodium borohydride in methanol.

The 3-(hydroxymethyl)imidazo[1,2-a]pyridine of Formula V may be converted to a 3-(halomethyl)imidazo[1,2-a]pyridine of Formula VI (where X is a halogen, preferably chlorine or bromine) by methods well known in the art. For example, reaction of a hydroxymethyl compound of Formula V with a suitable halogenating reagent in a suitable organic solvent will give the corresponding 3-(halomethyl)imidazo[1,2-a]-pyridine of Formula VI as a hydrohalide salt. Suitable halogenating agents include thionyl chloride, phosphorus oxychloride, oxalyl chloride, and the like. Suitable organic solvents for halogenation include alkanes and cycloalkanes; ethers and cyclic ethers; aromatic hydrocarbons; halocarbons, such as chloroform dichloromethane, ethylene dichloride, and the like; and other solvents known in the art. Preferred organic solvents include dichloromethane and chloroform. A related, and generally preferred, method involves heating a 3-(hydroxymethyl)imidazo[1,2-a]pyridine of Formula V in concentrated hydrochloric or hydrobromic acid at temperatures of 80° to 100°. See B. Beilenson and F. M. Hamer, J. Chem. Soc., 98–102 (1942). Scheme B illustrates a preferred method for preparing the sulfoxides of this invention, Formula I.

SCHEME B

Thio intermediates of Formula VIII may be prepared by S-alkylation of a 2-mercaptobenzimidazole of Formula VII with a 3-(halomethyl)imidazo[1,2-a]pyridine of Formula VI in a suitable organic solvent at room temperature. Suitable organic solvents for the reaction are organic liquids in which reactants may be dissolved or suspended but which are otherwise chemically inert. Examples of suitable organic solvents include N,N-dialkylformamides; lower alkanols, such as methanol, ethanol, propanol, isopropyl alcohol, and the like; and other solvents known in the art. Preferred organic solvents are absolute ethanol or isopropyl alcohol.

Thio intermediates of Formula VIII may form acid addition salts during the S-alkylation reaction. The corresponding neutral compounds of Formula VIII may be readily obtained by methods known to those skilled in the art. For example, treating an acid addition salt with a suitable base, followed by extraction into a suitable non-protic organic solvent, gives the free base form of the compound of Formula VIII. Suitable bases for neutralization include alkali metal hydroxides, such as lithium, sodium, or potassium hydroxide; alkali metal carbonates or bicarbonates, such as lithium, sodium, or potassium carbonate, or lithium, sodium, or potassium bicarbonte; and tertiary amines, such as triethylamine, tributylamine, N-methylmorpholine, and the like; and other such bases known in the art.

SCHEME B

VI or V

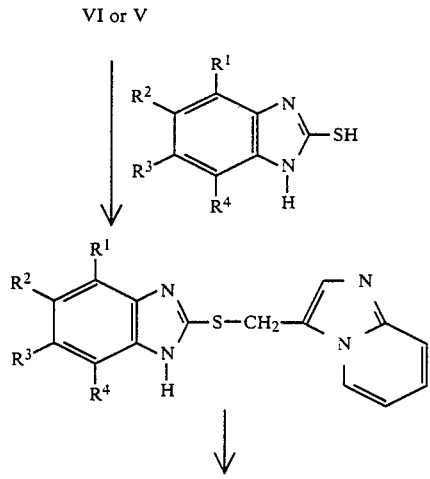

VII

VIII

-continued
SCHEME B

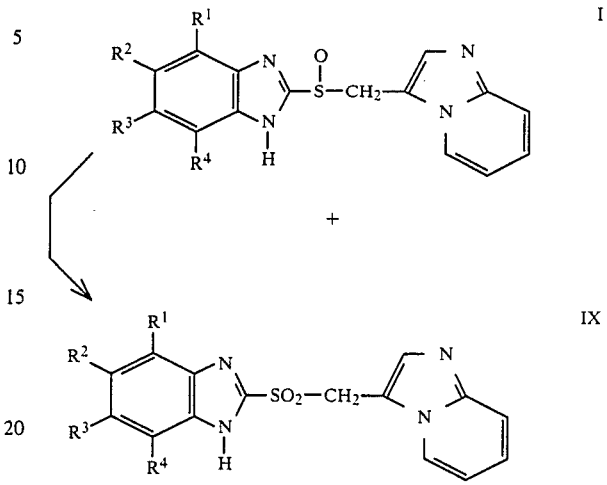

Preferred bases include sodium hydroxide or potassium hydroxide. Suitable non-protic organic solvents for extraction include alkanes and cycloalkanes; ethers and cyclic ethers; alkyl alkanoate esters, such as ethyl acetate and the like; aromatic hydrocarbons; halocarbons, such as chloroform, dichloromethane, ethylene dichloride, and the like; and other solvents known in the art. Preferred non-protic organic solvents include ethyl acetate, dichloromethane, and chloroform. Compounds that crystallize spontaneously upon addition of the organic solvent may be collected without completing the extraction procedure. If desired, compounds of Formula VIII may be purified by methods known in the art, including recrystallization and chromatography An alternative route for preparing thio intermediates of Formula VIII involves acid catalyzed S-alkylation of a 2-mercaptobenzimidazole of Formula VII with 3-(hydroxymethyl)imidazo[1,2-a]pyridine, Formula V. Preferred conditions include heating a mixture of compounds of Formulas V and VII in a suitable acidic medium. A suitable acidic medium is a chemical substance or mixture of chemical substances that dissolves the compounds of Formulas V and VII and is sufficiently acidic to induce the desired reaction, but which does not itself form significant quantities of byproducts by reaction with the compounds of Formulas V, and VII, and VIII. Preferred acidic media include mixtures of hydrogen halides such as hydrogen chloride or hydrogen bromide) in glacial acetic acid or aqueous hydrohalic acids (such as hydrochloric or hydrobromic acid) in acetic acid. After the reaction is quenched by pouring the mixture over ice and the mixture is neutralized with a suitable base (such as potassium carbonate), intermediates of Formula VIII may be isolated and purified by methods known in the art, including recrystallization and chromatography.

The sulfoxide compounds of this invention, Formula I, may be prepared by oxidation of the thio intermediates of Formula VIII using methods known to those skilled in the art. Commonly used oxidizing agents include, for example, peracids, such as m-chloroperoxybenzoic acid; peresters; peroxides, such as hydrogen peroxide; sodium metaperiodate; selenium dioxide; manganese dioxide; iodosobenzene; and the like. Preferred conditions for preparing sulfoxides of Formula I include oxidizing intermediates VIII with an approximately equimolar quantity of m-chloroperoxybenzoic acid in a suitable organic solvent at temperatures below 0°. Suitable organic solvents for the oxidation include alkanes and cycloalkanes; aromatic hydrocarbons; halocarbons such as chloroform, dichloromethane, ethylene dichloride, and the like; and other solvents known in the art. A preferred organic solvent is dichloromethane. Oxidization is then quenched by adding dimethylsulfide. The sulfoxides of Formula I may then be isolated and purified by methods known in the art, including recrystallization and chromatography.

Further oxidation of the sulfoxide compounds of Formula I yields corresponding sulfones of Formula IX. The sulfones may form in situ during the initial oxidation reaction of thio intermediates of Formula VIII or may be prepared by a separate oxidation of isolated sulfoxides of Formula I. The sulfones of Formula IX may then be isolated and purified by methods known in the art, including recrystallization and chromatography. Where the sulfones of Formula IX are prepared along with sulfoxides of Formula I during the initial oxidation reaction, the preferred method of isolation is chromatography.

Acid addition salts of this invention may be prepared during the course of the reactions (as described above), by ion exchange from those salts using methods known in the art, or by acidification of free bases of the compounds. Base addition salts of this invention may be prepared using methods known in the art, including those methods disclosed in British patent No. 2,137,616.

Although some 2-mercaptobenzimidazoles of Formula VII (used as described above; see Scheme B) are commercially available, they may also be prepared by methods known to those skilled in the art. For example, Scheme C illustrates the preparation of 2-mercaptobenzimidazoles from substituted diaminobenzenes of Formula X.

SCHEME C

A preferred cyclization method employs an alkali metal alkylxanthate salt of the formula alkyl-O(C=O)S⁻M⁺, where M⁺ represents an alkali metal ion. Such alkylxanthate salts may be preformed by methods known in the art or may be formed in situ by mixing an alkali metal hydroxide (preferably sodium hydroxide) and carbon disulfide in an alcohol (preferably ethanol). Preferred cyclization conditions include heating an aqueous or alcoholic mixture of a diaminobenzene of Formula X with sodium or potassium ethylxanthate at reflux under an inert atmosphere, such as argon.

The preferred embodiments of this invention include compounds of the following general structure:

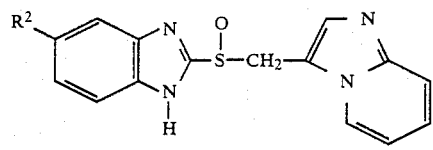

XI or the pharmaceutically acceptable acid addition salts thereof; wherein $R^1$, $R^2$, and $R^3$, are independently hydrogen, methyl, methoxy, trifluoromethyl, or chlorine.

SCHEME C

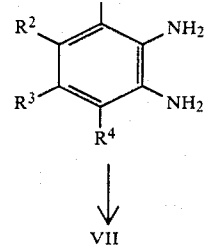

X

VII

A most preferred embodiment of this invention includes a compound of the following structure:

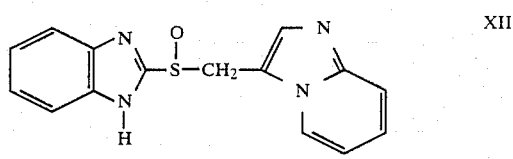

XII or the pharmaceutically acceptable acid addition salts thereof.

The compounds of this invention exhibited gastric antisecretory activity in canines, as indicated by inhibition in vitro of $(H^+ + K^+)$-ATPase obtained from canine gastric mucosa. The antisecretory activity of the compounds of this invention illustrated in the Examples was tested by the following method.

Inhibition of $(H^{30} + K^+)$-ATPase from Canine Gastric Mucosa

Mongrel dogs weighing 15 to 25 kilograms were fasted for twenty-four hours, with water provided ad libitum. The animals were anesthetized with pentobarbital and the stomachs were removed. Subsequent tissue manipulations and subcellular fractionations were performed at 0° to 4° C. After the stomachs were cut open and rinsed with tap water, the antral and cardiac regions were removed and the remaining tissue was rinsed three times in saline. The glandular mucosa was removed mechanically, chopped finely in a medium containing 10 mM Tris hydrochloride (pH 7.4) and 250 mM sucrose, and homogenized. The homogenate was centrifuged at 20,000×g for twenty minutes and the pellet discarded. The supernatant was then centrifuged at 150,000×g for ninety minutes and the supernatant discarded. The pellet was resuspended in the Tris-HCl/sucrose medium by homogenization. Part (2 ml) of the resultant microsomal suspension was layered onto a step gradient consisting of 9 ml of 15% sucrose above 12 ml of 30% sucrose, each sucrose solution being buffered with 10 mM Tris hydrochloride (pH 7.4) containing 0.01% sodium azide. The microsomes retained at the 15–30% sucrose interface, after centrifugation at 250,000×g for sixty minutes, were used as the source of $(H^+ + K^+)$-ATPase. Microsomal preparations were lyophilized, a process that assured potassium ion permiability, and stored at −10° until used.

The $(H^+ + K^+)$-ATPase activity for each test compound was determined, in duplicate, by measuring the release of inorganic phosphate, which was assayed according to the method of J. ChandraRajan and L. Klein., *Anal. Biochem.*, 72. 407–412 (1976). The $(H^+ + K^+)$-ATPase assay medium consisted of 20 mM Mes-Tris (pH 6.0), 5 mM magnesium chloride, 25 mM sucrose, and 4mM Tris-ATP with or without 20 mM potassium chloride in a total volume of 2 ml. Microsomal suspensions (20 to 60 mcl, containing about 25 mcg protein) were added to the assay medium, without Tris-ATP, and then preincubated with a test compound for thirty minutes at 37°. The assay was initiated by adding Tris-ATP and the mixture was incubated another thirty minutes at 37°. A 200-mcl aliquot of the assay mixture was then added to 1.4 ml of a solution consisting of 0.1 M sodium acetate (pH 4.0) and 10% sodium dodecylsulfate, followed by the addition of 200 mcl each Of 1% ammonium molybdate and 1% ascorbic aoid. At least fifteen minutes later, the optical absorbance at 870 nm (which was proportional to inorganic phosphate concentration up to 100 nmoles per tube, as determined by a standard curve) was obtained. Enzyme activity was linear with incubation time.

$(H^+ + K^+)$-ATPase activity is represented by the difference between the measured activities in the presence of potassium ion ($K^+$-stimulated) and in the absence of potassium ion (basal). The concentration of a test compound required to inhibit 50% of the $(H^+ + K^+)$-ATPase activity (i.e., the $IC_{50}$) was determined at least in duplicate using linear regression analysis of results obtained for three different compound concentrations ranging from 0.1 mcM to 0.2 mM. If the $IC_{50}$ for a test compound could not be determined for the concentration range tested, percent inhibition of $(H^+ + K^+)$-ATPase was obtained for the compound at 0.1 mM. Test results are summarized in Table I.

TABLE I

| $(H^+ + K^+)$-ATPase Inhibition Test Results. | |
|---|---|
| Compound [Product of Example No.] | $(H^+ + K^+)$-ATPase $IC_{50}$ (mcM) |
| 2 | 3.88 |
| 4 | >100 |

By virtue of their $(H^+ + K^+)$-ATPase inhibitory activity, the compounds of Formula I are useful in treating ulcers in mammals. A physician or veterinarian of ordinary skill can readily determine whether a subject has ulcers. Regardless of the route of administration selected, the compounds of the present invention are formulated into pharmaceutically acceptable dosage forms by conventional methods known to those skilled in the art. The compounds may be formulated using pharmacologically acceptable acid addition or base addition salts. Moreover, the compounds or their salts may be used in a suitable hydrated form.

The compounds can be administered in such oral dosage forms as tablets, capsules, pills, powders, granules, elixirs, or syrups. The compounds may also be administered intravascularly, intraperitoneally, subcutaneously or intramuscularly, using forms known to the pharmaceutical art. In general, the preferred form of administration is oral. For the orally administered pharmaceutical compositions and method of the present invention, tbe foregoing active ingredients will typically be administered in admixture with suitable pharmaceutical diluents excipients, or carriers (collectively referred to herein as "carrier" materials) suitably selected with respect to the intended form of administration, that is, oral tablets, capsules, elixirs, syrups, and the like, and consistent with conventional pharmaceutical practices. For example, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like, or various combinations thereof; for oral administration in liquid form, the active drug components may be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride and the like, or combinations thereof. Disintegrators include, without limitation, starch, methylcellulose, agar, bentonite guar gum, and the like, or combinations thereof. Sweetening and flavoring agents and preservatives can also be included where appropriate.

For intravascular, intraperitoneal, subcutaneous, or intramuscular administration active drug components may be combined with a suitable carrier such as water, saline, aqueous dextrose, and the like.

By whatever route of administration selected, an effective but non-toxic quantity of the compound is employed in treatment. The dosage regimen for preventing or treating ulcers with the compounds of this invention is selected in accordance with a variety of factors, including the type, age, weight, sex, and medical condition of the patient; the severity of the condition, the route of administration, and the particular compound employed. An ordinarily skilled physician or veterinarian can readily determine and prescribe the effective amount of the drug required to prevent or arrest the progress of the condition. In so proceeding, the physician or veterinarian could employ relatively low doses at first and subsequently increase the dose until a maximum response is obtained. Dosages of the compounds of the invention may be in the range of about 1.0 mcg/kg to 800 mg/kg, preferably in the range of about 10 to 100 mg/kg orally or about 1.0 to 20 mg/kg intravenously.

The following examples further illustrate details for the preparation of the compounds of this invention. The invention, which is set forth in the foregoing disclosure is not to be construed or limited either in spirit or in scope by these examples. Those skilled in the art will readily understand that known variations of the conditions and processes of the following preparative procedures can be used to prepare these compounds. All temperatures are degrees Celsius unless otherwise noted. Chromatographic isolation and purification of the compounds of this invention, where required, was effected using silica gel or basic alumina, with mixtures of ethyl acetate and hexane or ethanol and dichloromethane used as eluent (unless otherwise specified). The appropriate chromatographic system was chosen for each compound by comparing separations on thin layer chromatography plates coated with silica gel or basic alumina.

DESCRIPTION OF THE PREFERRED EMBODIMENTS

Example 1

2-[(imidazo[1,2-a]pyridin-3-ylmethyl)thio]-1H-benzimidazole

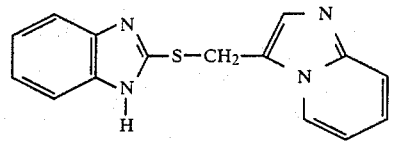

A mixture of 9.4 g (0.1 mole) of 2-aminopyridine and 19.2 g (0.11 mole) of 45% aqueous chloroacetaldehyde was stirred, during which spontaneous heating occurred. When the exothermic reaction subsided, the mixture was dissolved in methanol containing 15 ml of concentrated aqueous ammonia and extracted with dichloromethane. The organic layer was dried over magnesium sulfate, filtered, and concentrated in vacuo to an oil. Distillation at 80-83° and 0.2 mm Hg pressure yielded 10.5 g of imidazo[1,2-a]pyridine as an oil. A solution of 9.5 g (80.5 mmole) of imidazo[1,2-a]pyridine in 60 ml of dimethylformamide was heated to 90°. Phosphorus oxychloride (9.27 ml, ca. 100 mmole) was added dropwise over a twenty minute period, and the mixture was stirred at 90° for two hours and at room temperature for an additional twenty hours. The mixture was diluted with 60 ml of water and made basic with 30% aqueous sodium hydroxide. The resultant solid was collected by filtration, washed with water, and air dried to yield 1.8 g of 3-imidazo[1,2-a]pyridinecarboxaldehyde as the analytically pure ¼ hydrate. [Calcd. for $C_8H_6N_2O.H_2O$: C, 58.53; H, 3.68; N, 17.06. Found: C, 58.77; H, 3.68; N, 17.48.]To a solution of 1.6 g (10 mmole) of 3-imidazo[1,2-a]-pyridinecarboxaldehyde in 15 ml of methanol was added 204 mg (5.4 mmole) of sodium borohydride. After one hour the mixture was acidified with concentrated hydrochloric acid and then concentrated in vacuo. Recrystallization of the residue from ethanol yielded 707 mg of 3-hydroxymethylimidazo[1,2-a]pyridine as the hydrochloride salt. A 500 mg (2.7 mmole) portion of the hydroxymethyl compound was dissolved in 3.0 ml of concentrated hydrochloric acid and heated at 80° for one hour. The mixture was concentrated in vacuo and the residue was recrystallized from isopropyl alcohol to yield 465 mg of 3-chloromethylimidazo[1,2-a]pyridine as the hydrochloride salt. A mixture of 390 mg (1.92 mmole) of the chloromethyl compound and 288 mg (1.92 mmole) of 2-mercaptobenzimidazole in 7 ml of isopropyl alcohol was stirred for one hour. The precipitate that formed was collected and partitioned between 5% aqueous sodium hydroxide and dichloromethane. The organic layer was washed with water, dried over magnesium sulfate, filtered and concentrated in vacuo. Trituration of the residue with diethyl ether yielded the title compound as an analytically pure solid. Structure assignment was supported by the nmr spectrum and by elemental analysis.

Analysis Calcd for $C_{15}H_{12}N_4S$: C, 64.27; H, 4.31; N, 19.98; S, 11.44.

Found: C, 64.27; H, 4.50; N, 20.03; S, 11.43.

Example 2

2-[(imidazo[1,2-a]pyridin-3-ylmethyl)sulfinyl]-1H-benzimidazole ¼ hydrate

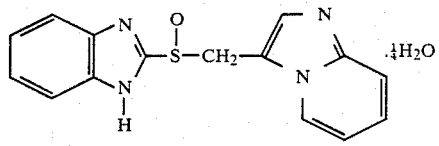

A suspension of 150 mg (0.54 mmole) of 2-[(imidazo[1,2-a]pyridin-3-ylmethyl)thio]-1H-benzimidazole (see Example 1) in 4.0 ml of dichloromethane was cooled in an ice bath. A solution of 120 mg (0.59 mmole) of ca. 85% m-chloroperbenzoic acid in the minimum amount of dichloromethane needed to form a solution was then added dropwise with stirring. The reaction was quenched with a few drops of dimethylsulfide. The mixture was washed with saturated aqueous sodium bicarbonate. The organic phase was concentrated in vacuo and chromatographed on silica gel (using ethanol-dichloromethane-triethylamine as eluent) to yield 35 mg of the title compound. Structure assignment was supported by the nmr and infrared spectra and by elemental analysis.

Analysis Calcd. for $C_{15}H_{12}N_4SO$. 1 ¼$H_2O$: C. 59.88; H, 4.18; N, 18.62; S, 10.65. Found: C, 59.95; H, 4.02; S, 18.73; S, 10.69.

Example 3

2-[(imidazo[1,2-a]pyridin-2-ylmethyl)thio]-1H-benzimidazole

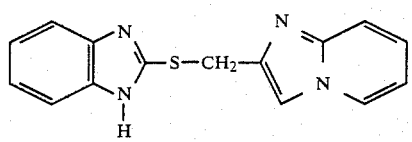

A mixture of 4.7 g (0.05 mole) of 2-aminopyridine and 6.4 g (0.05 mole) of 1,3-dichloropropan-2-one in 50 ml of ethanol was stirred overnight at room temperature. The mixture was concentrated in vacuo and the residue was triturated with acetonitrile. The solid that formed was recrystallized from acetonitrile-methanol to yield ca. 1 g of 2-chloromethylimidazo[1,2-a]pyridine as the hydrated hydrochloride salt. [Calcd. for $C_8H_7N_2Cl.HCl.H_2O$: C, 43.42; H, 4.52; N, 12.67; Cl, 32.12. Found: C, 42.94; H, 4.62; N, 12.68; Cl, 32.12.] A mixture of 790 mg (3.89 mmole) of the chloromethyl compound and 585 mg (3.90 mmole) of 2-mercaptobenzimidazole in 200 ml of isopropyl alcohol was stirred for two days. The mixture was concentrated in vacuo and the residue was dissolved in boiling isopropyl alcohol. The precipitate that formed upon cooling was collected and partitioned between saturated aqueous sodium bicarbonate and chloroform. The organic layer was dried over magnesium sulfate, filtered and concentrated in vacuo to a solid. Recrystallization from isopropyl alcohol yielded (in two crops) 500 mg of the title compound as an analytically pure solid, m.p. 220°-222°. Structure assignment was supported by the nmr and infrared spectra and by elemental analysis.

Analysis. Calcd. for $C_{15}H_{12}N_4S$: C, 64.27; H, 4.31; N, 19.98; S, 11.44. Found: C, 64.24; H, 4.35; N, 20.29; S, 11.59.

Example 4

2-[(imidazo[1,2-a]pyridin-2-ylmethyl)sulfinyl]-1H-benzimidazole

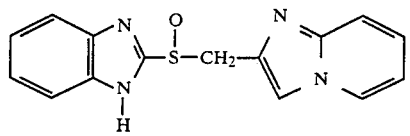

The title compound, m.p. 195°–196°, was prepared by the method described in Example 2 using 345 mg of 2-[(imidazo[1,2-a]pyridin-2-ylmethyl)thio]-1H-benzimidazole instead of 2-[(imidazo[1,2-a]pyridin-3-ylmethyl)thio]-1H-benzimidazole and chloroform instead of dichloromethane. Structure assignment was supported by the nmr and infrared spectra and by elemental analysis. Analysis. Calcd. for $C_{15}H_{12}N_4SO$: C, 60.80; H, 4.08; N, 18.91; S, 10.82. Found: C, 60.73; H, 4.18; N, 18.75; S, 10.68.

Example 5

2-[(imidazo[1,2-a]pyridin-3-ylmethyl)thio]-5-methyl-1H-benzimidazole ¼ hydrate

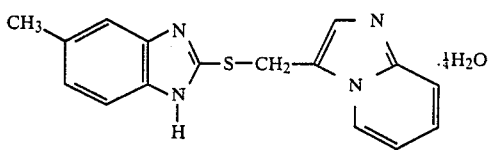

A mixture of 903 mg (5.5 mmole) of 2-mercapto-5-methylbenzimidazole and 805 mg (5.4 mmole) of 3-hydroxymethylimidazo[1,2-a]pyridine (prepared as in Example 1) was dissolved in 10 ml of 48% aqueous hydrobromic acid and 10 ml of acetic acid and heated to reflux. After being cooled to room temperature, the mixture was poured into water and made alkaline with potassium carbonate. The oil that separated was extracted into dichloromethane, washed with water, dried over magnesium sulfate, filtered, and concentrated to an oil that crystallized on standing. The solid was collected by filtration, washed with diethyl ether, and air dried to yield the title compound as 610 mg of analytically pure solid. Structure assignment was supported by the nmr and infrared spectra and by elemental analysis.

Analysis. Calcd. for $C_{16}H_{14}N_4S \cdot \frac{1}{4}H_2O$: C, 64.29; H, 4.89; N, 18.78; S, 10.72. Found: C, 64.57; H, 4.77; N, 18.76; S, 10.84.

Example 6

2-[(imidazo[1,2-a]pyridin-3-ylmethyl)sulfinyl]-5-methyl-1H-benzimidazole

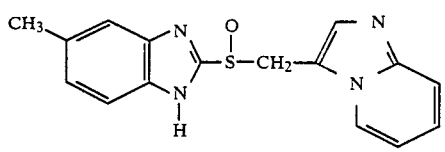

The title compound was prepared by the method described in Example 2 using 508 mg of 2-[(imidazo[1,2-a]pyridin-3-ylmethyl)thio]-5-methyl-1-benzimidazole instead of 2-[(imidazo[1,2-a]pyridin-3-ylmethyl)thio]-1-benzimidazole. Structure assignment was supported by the nmr and infrared spectra and by elemental analysis.

Analysis. Calcd. for C : C, 61.92; H, 4.55; N, 18.05; S, 10.33. Found: C, 62.09; H, 4.67; N, 18.08; S, 9.96.

Example 7

2-[(imidazo[1,2-a]pyridin-3-ylmethyl)thio]-5-methoxy-1H-benzimidazole

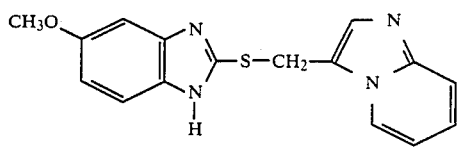

The title compound was prepared by the method described in Example 5 using 991 mg of 2-mercapto-5-methoxybenzimidazole instead of 2-mercapto-5-methylbenzimidazole. Structure assignment was supported by the nmr and infrared spectra.

Example 8

2-[(imidazo[1,2-a]pyridin-3-ylmethyl)sulfinyl]-5-methoxy-1H-benzimidazole ¾ hydrate

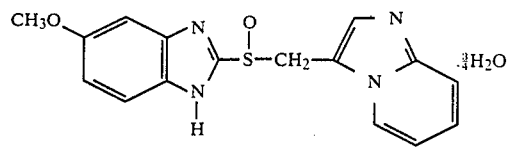

The title compound was prepared by the method described in Example 2 using 250 mg of 2-[(imidazo[1,2-a]pyridin-3-ylmethyl)thio]-5-methoxy-1-benzimidazole instead of 2-[(imidazo[1,2-a]pyridin-3-ylmethyl)thio]-1-benzimidazole. Structure assignment was supported by the nmr and infrared spectra and by elemental analysis.

Analysis. Calcd. for $C_{16}H_{14}N_4SO_2 \cdot \frac{3}{4}H_2O$: C, 56.53; H, 4.59; N, 16.48; S, 9.43. Found: C, 56.31; H, 4.25; N, 16.28; S, 9.66.

Example 9

5-chloro-2-[(imidazo[1.2-a]pyridin-3-ylmethyl)thio]-1-benzimidazole

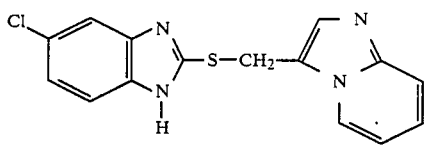

The title compound was prepared by the method described in Example 5 using 1.01 g of 5-chloro-2-mercaptobenzimidazole instead of 2-mercapto-5-methylbenzimidazole. Structure assignment was supported by the nmr and infrared spectra.

Example 10

5-chloro-2-[(imidazo[1,2-a]pyridin-3-ylmethyl)sulfinyl]-1H-benzimidazole

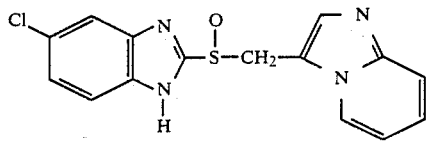

The title compound was prepared by the method described in Example 2 using 515 mg of 5-chloro-2-[(imidazo[1,2-a]pyridin-3-ylmethyl)thio]-5-methoxy-1H-bezimidazole instead of 2-[(imidazo[1,2-a]pyridin-3-ylmethyl)thio]-1H-benzimidazol. Structure assignment was supported by the nmr and infrared spectra and by elemental analysis.

Analysis. Calcd. for $C_{15}H_{11}N_4SOCl$ C, 53.37; H, 3.39; N, 16.60; S, 9.49.

Found: C, 53.63; H, 3.61; N, 16.24; S, 9.40.

Example 11

2-[(imidazo[1,2-a]pyridin-3-ylmethyl)thio]-5-(trifluoromethyl)-1-benzimidazole

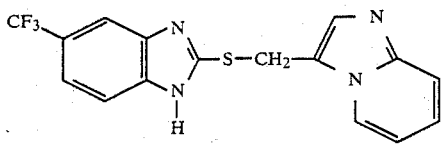

The title compound was prepared by the method described in Example 5 using 1.2 g of 2-mercapto-5-(trifluoromethyl)benzimidazole instead of 2-mercapto-5-methylbenzimidazole. Structure assignment was supported by the nmr and infrared spectra and by elemental analysis.

Analysis. Calcd. for $C_{16}H_{11}N_4SF_3$: C, 55.16; H, 3.13; N, 16.08.

Found: C, 55.15; H, 3.16; N, 15.99.

Example 12

2-[(imidazo[1,2-a]pyridin-3-ylmethyl)sulfinyl]-5-(trifluoromethyl)-1-benzimidazole ¼ ethanol solvate

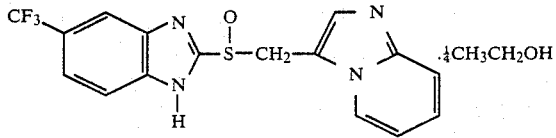

The title compound was prepared by the method described in Example 2 using 1.3 g of 2-[(imidazo[1,2-a]pyridin-3-ylmethyl)thio]-5-(trifluoromethyl)-1-benzimidazole instead of 2-[(imidazo[1,2-a]pyridin-3-ylmethyl)thio]-1-benzimidazole. Structure assignment was supported by the nmr and infrared spectra and by elemental analysis.

Analysis. Calcd. for $C_{16}H_{11}N_4SOF_3 \cdot \frac{1}{4}CH_3CH_2OH$: C, 51.66; H, 3.33; N, 14.49; S, 8.29.

Found: C, 51.69; H, 3.29; N, 14.41; S, 8.61.

What is claimed is:

1. A compound of the formula;

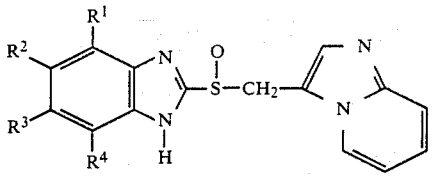

or a pharmaceutically acceptable addition salt thereof; wherein $R^1$, $R^2$, $R^3$ and $R^4$ are independently:
 (a) hydrogen;
 (b) $C_1$–$C_6$ alkyl;
 (c) $C_1$–$C_6$ alkyoxy;
 (d) fluorinated $C_1$–$C_4$ alkyl; or
 (e) halogen.

2. A compound according to claim 1 having the formula;

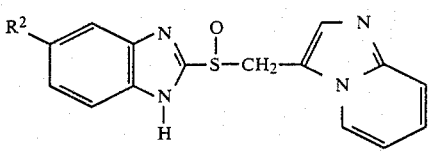

or a pharmaceutically acceptable addition salt thereof; wherein $R^2$ is:
 (a) hydrogen;
 (b) $C_1$–$C_6$ alkyl;
 (c) $C_1$–$C_6$ alkoxy;
 (d) fluorinated $C_1$–$C_4$ alkyl; or
 (e) halogen.

3. A compound according to claim 2, which is 2-[(imidazo[1,2-a]pyridin-3-ylmethyl)sulfinyl]-1-benzimidazole.

4. A compound according to claim 2, which is 2-[(imidazo[1,2-a]pyridin-3-ylmethyl)sulfinyl]-5-methyl-1H-benzimidazole.

5. A compound according to claim 2, which is 2-[(imidazo[1,2-a]pyridin-3-ylmethyl)sulfinyl]-5-methoxy-1-benzimidazole.

6. A compound according to claim 2, which is 5-chloro-2-[(imidazo[1,2-a]pyridin-3-ylmethyl) sulfinyl]-1-benzimidazole.

7. A compound according to claim 2, which is 2-[(imidazo[1,2-a]pyridin-3-ylmethyl)sulfinyl-5-(trifluoromethyl)-1H-benzimidazole.

8. A pharmaceutical composition comprising at least one compound according to claim 1, together with one or more non-toxic pharmaceutically acceptable carriers.

9. A pharmaceutical composition according to claim 8 wherein said compound is selected from the group consisting of:
2-[(imidazo[1,2-a]pyridin-3-ylmethyl)sulfinyl]-1-benzimidazole,
2-[(imidazo[1,2-a]pyridin-3-ylmethyl)sulfinyl]-5-methyl-1-benzimidazole,
2-[(imidazo[1,2-a]pyridin-3-ylmethyl)sulfinyl]-5-methoxy-1-benzimidazole,
5-chloro-2-[(imidazo[1,2-a]pyridin-3-ylmethyl)sulfinyl]-1H-benzimidazole, and
2-[(imidazo[1,2-a]pyridin-3-ylmethyl)sulfinyl]-5-[trifluoromethyl)-1-benzimidazole.

10. A method for treating ulcers in mammals comprising administering a therapeutically effective amount of at least one compound of claim 1 to a mammal in need of such treatment.

11. A method according to claim 10 wherein said compound is selected from the group consisting of:

2-[(imidazo[1,2-a]pyridin-3-ylmethyl)sulfinyl]-1-benzimidazole,

2-[(imidazo[1,2-a]pyridin-3-ylmethyl)sulfinyl]-5-methyl-1-benzimidazole,

2-[(imidazo[1,2-a]pyridin-3-ylmethyl)sulfinyl]-5-methoxy-1-benzimidazole, 5-chloro-2-[(imidazo[1,2-a]pyridin-3-ylmethyl)sulfinyl]-1-benzimidazole, and 2-[(imidazo[1,2-a]pyridin-3-ylmethyl)sulfinyl]-5-(trifluoromethyl)-1-benzimidazole.

12. A method for treating ulcers in mammals comprising administering a therapeutically effective amount of a pharmaceutical compositon of claim 8 to a mammal in need of such treatment.

* * * * *

UNITED STATES PATENT AND TRADEMARK OFFICE
CERTIFICATE OF CORRECTION

Page 1 of 5

PATENT NO. : 4,721,718
DATED : January 26, 1988
INVENTOR(S) : Adelstein, et al.

It is certified that error appears in the above-identified patent and that said Letters Patent is hereby corrected as shown below:

Column 1, line 15, reading "$(H^{30} + K^+)$-ATPase" should read -- $(H^+ + K^+)$-ATPase --.

Column 8, line 34, reading "$(H^{30} + K^+)$-ATPase" should read -- $(H^+ + K^+)$-ATPase --.

Column 14, line 1, reading "-5-methyl-1-benzimidazole" should read -- -5-methyl-1H-benzimidazole --.

Column 14, line 2, reading "-ylmethyl)thio]-1-" should read -- -ylmethyl)thio]-1H- --.

Column 14, line 6, reading "Analysis. Calcd. for C : C," should read -- Analysis. Calcd. for $C_{16}H_{14}N_4SO$: C, --.

UNITED STATES PATENT AND TRADEMARK OFFICE
CERTIFICATE OF CORRECTION

PATENT NO. : 4,721,718

DATED : January 26, 1988

INVENTOR(S) : Adelstein, et al.

It is certified that error appears in the above-identified patent and that said Letters Patent is hereby corrected as shown below:

Column 14, line 42, "-methoxy-1-benzimidazole" should read
-- -methoxy-1H-benzimidazole --.

Column 14, line 43, reading "-ylmethyl)thio]-1-" should read
-- -ylmethyl)thio]-1H- --.

Column 14, line 53, reading "-ylmethyl)thio]-1-" should read
-- -ylmethyl)thio]-1H- --.

Column 15, line 26, reading "-1-benzimidazole" should read
-- -1H-benzimidazole --.

Column 15, line 48, reading "-1-benzimidazole" should read
-- -1H-benzimidazole --.

UNITED STATES PATENT AND TRADEMARK OFFICE
CERTIFICATE OF CORRECTION

PATENT NO. : 4,721,718

DATED : January 26, 1988

INVENTOR(S) : Adelstein, et al.

It is certified that error appears in the above-identified patent and that said Letters Patent is hereby corrected as shown below:

Column 15, lines 59-60, reading "-1-benzimidazole" should read -- -1H-benzimidazole --.

Column 15, line 61, reading "-1-benzimidazole" should read -- -1H-benzimidazole --.

Column 16, lines 36-37, reading "-1-benzimidazole" should read -- -1H-benzimidazole --.

Column 16, line 43, reading "-1-benzimidazole" should read -- -1H-benzimidazole --.

Column 16, line 46, reading "-1-benzimidazole" should read -- -1H-benzimidazole --.

UNITED STATES PATENT AND TRADEMARK OFFICE
CERTIFICATE OF CORRECTION

PATENT NO. : 4,721,718

DATED : January 26, 1988

INVENTOR(S) : Adelstein, et al.

It is certified that error appears in the above-identified patent and that said Letters Patent is hereby corrected as shown below:

Column 16, lines 57-58, reading "-1-benzimidazole" should read -- -1H-benzimidazole --.

Column 16, line 60, reading "-1-benzimidazole" should read -- -1H-benzimidazole --.

Column 16, line 62, reading "-1-benzimidazole" should read -- -1H-benzimidazole --.

Column 16, line 66, reading "-1-benzimidazole" should read -- -1H-benzimidazole --.

Column 17, Line 7-8, reading "-1-benzimidazole" should read -- -1H-benzimidazole --.

UNITED STATES PATENT AND TRADEMARK OFFICE
CERTIFICATE OF CORRECTION

PATENT NO. : 4,721,718
DATED : January 26, 1988
INVENTOR(S) : Adelstein, et al.

It is certified that error appears in the above-identified patent and that said Letters Patent is hereby corrected as shown below:

Column 17, line 11, reading "-1-benzimidazole" should read -- -1H-benzimidazole --.

Column 18, line 2, reading "-1-benzimidazole" should read -- -1H-benzimidazole --.

Column 18, line 4, reading "1-benzimidazole" should read -- 1H-benzimidazole --.

Column 18, line 6, reading "-1-benzimidazole" should read -- -1H-benzimidazole --.

Signed and Sealed this

Fourth Day of June, 1991

Attest:

HARRY F. MANBECK, JR.

Attesting Officer

Commissioner of Patents and Trademarks